(12) United States Patent
Pfefferle et al.

(10) Patent No.: US 6,730,091 B1
(45) Date of Patent: May 4, 2004

(54) BLOCKABLE BONE PLATE

(75) Inventors: Joachim Pfefferle, Munstertal (DE); Michael Roth, Freiburg (DE); Peter Scheuble, Wasenweiler (DE); Hermann Zeuner, Freiburg (DE)

(73) Assignee: Medartis AG, Basel (CH)

( * ) Notice: Subject to any disclaimer, the term of this patent is extended or adjusted under 35 U.S.C. 154(b) by 0 days.

(21) Appl. No.: 09/959,653

(22) PCT Filed: May 3, 2000

(86) PCT No.: PCT/CH00/00247

§ 371 (c)(1), (2), (4) Date: Nov. 2, 2001

(87) PCT Pub. No.: WO00/66012

PCT Pub. Date: Nov. 9, 2000

(30) Foreign Application Priority Data

May 3, 1999 (CH) .............................................. 0830/99

(51) Int. Cl.[7] .............................................. A61B 17/56
(52) U.S. Cl. .............................. 606/70; 606/69; 606/73; 606/71
(58) Field of Search .............................. 606/70, 69, 71, 606/72, 73, 104, 60, 62, 64

(56) References Cited

U.S. PATENT DOCUMENTS

| 4,966,599 | A | * | 10/1990 | Pollock ........................ 606/69 |
| 5,607,428 | A | * | 3/1997 | Lin .............................. 606/69 |
| 5,709,686 | A | * | 1/1998 | Talos et al. ................... 606/69 |
| 5,807,396 | A | | 9/1998 | Raveh |
| 6,129,728 | A | * | 10/2000 | Schumacher et al. ......... 606/71 |
| 6,322,562 | B1 | * | 11/2001 | Wolter .......................... 606/69 |
| 6,325,803 | B1 | * | 12/2001 | Schumacher et al. ......... 606/71 |
| 6,423,068 | B1 | * | 7/2002 | Reisberg et al. .............. 606/69 |

FOREIGN PATENT DOCUMENTS

| DE | 19629011 | 1/1998 |
| WO | WO 00/36984 | 6/2000 |

\* cited by examiner

*Primary Examiner*—Pedro Philogene
(74) *Attorney, Agent, or Firm*—Leydig, Voit & Mayer, Ltd.

(57) ABSTRACT

The blockable bone plate consists of a plurality of plate members which are connected to each other via webs. A screw hole is provided in at least some plate members, preferably in each plate member. The screw hole is surrounded by a spherical countersink on the upper surface of the plate. Provided internally in the screw hole there is an engagement contour which consists of contour valleys and contour peaks partially running in a horizontal and radial peripheral direction on the wall of the screw hole. The engagement contour is preferably produced by milling and has for example a pointed, round, trapezoidal or serrated configuration. A blocking thread is provided under the screw head of the screw intended for blocking. As the screw is screwed in, the blocking thread engages in the engagement contour. The particular advantages lie in increased security against the screw coming loose and in the possibility of also inserting the screw through the plate at an inclination. Furthermore, a bone plate is proposed which has the shape of an arc of a circle in the longitudinal axis of the plate and which requires less bending, particularly on the human lower jaw, and adapts to the bone in a more ideal manner.

32 Claims, 13 Drawing Sheets

Fig. 1A 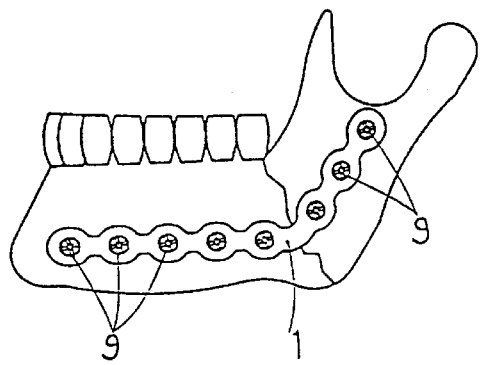 Fig. 1B 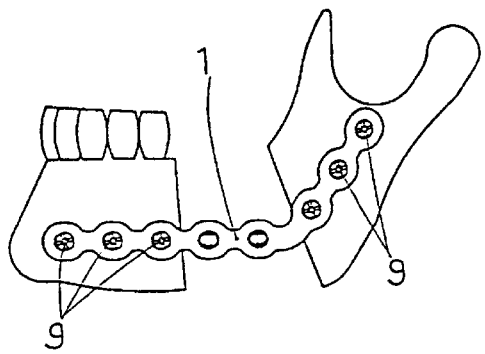
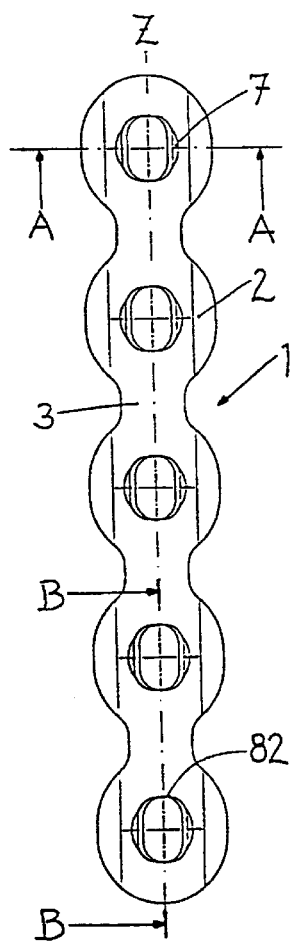 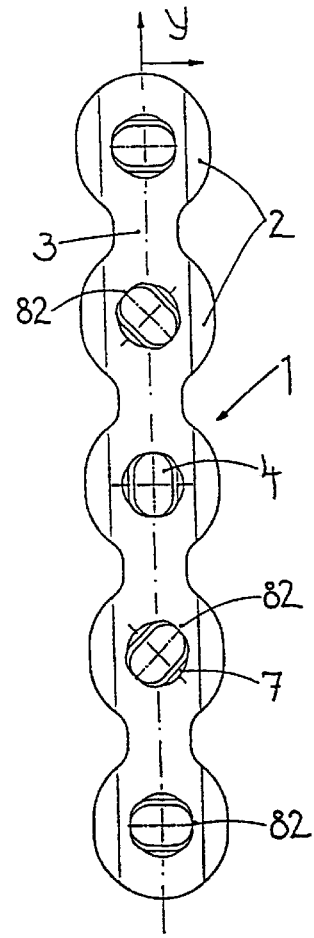
Fig. 2A  Fig. 2B

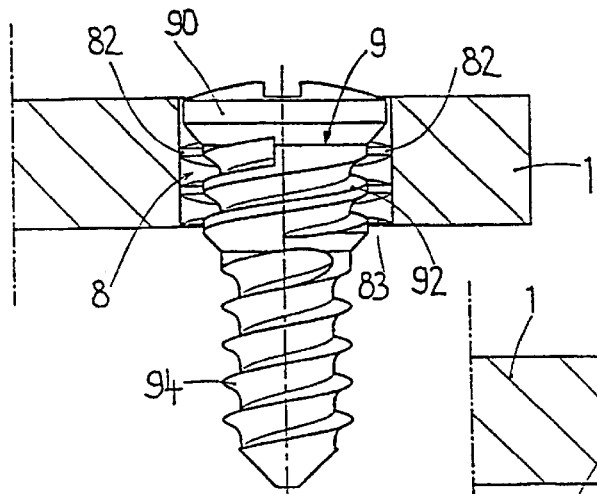
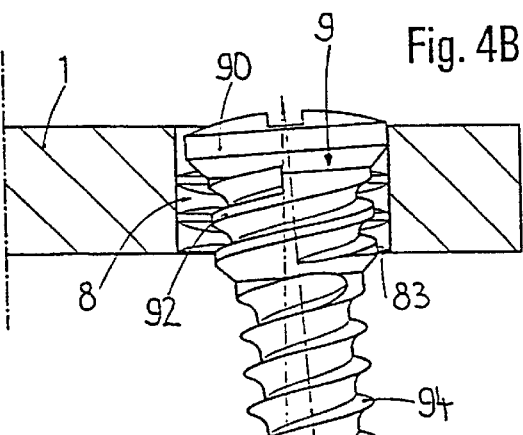
Fig. 4A
Fig. 4B
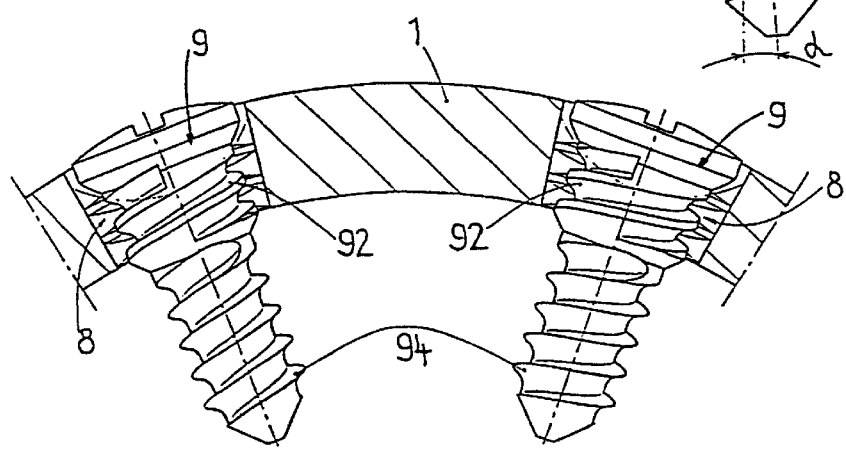
Fig. 4C
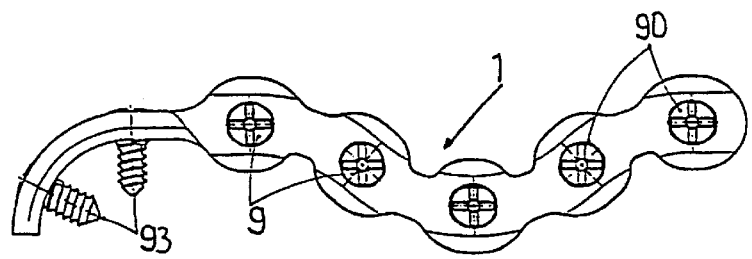
Fig. 4D

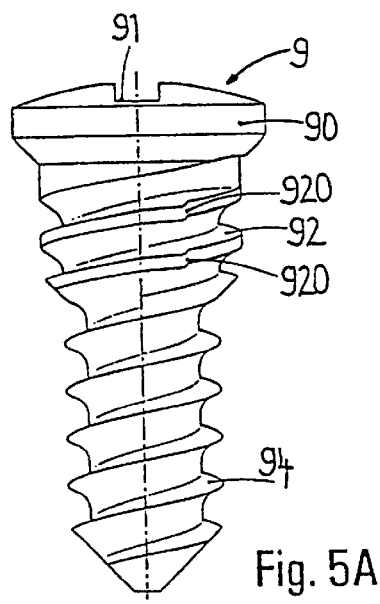
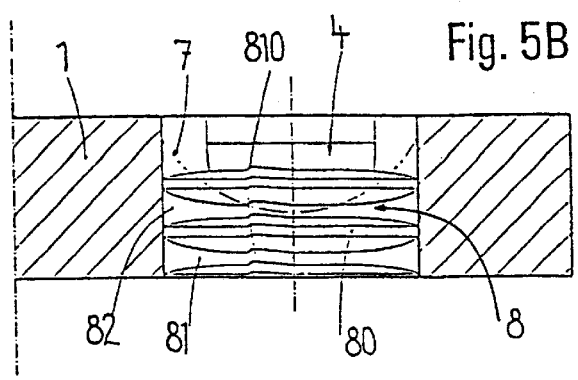
Fig. 5A
Fig. 5B
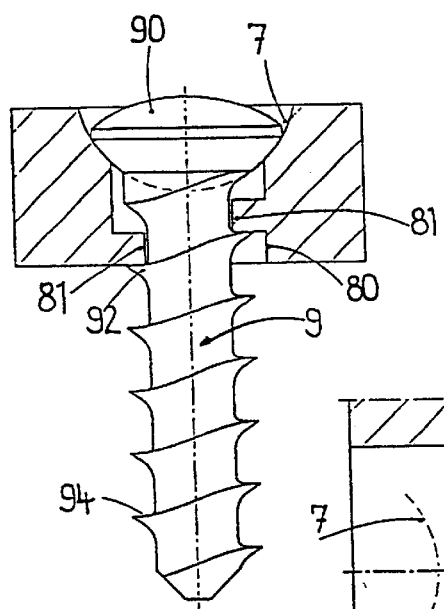
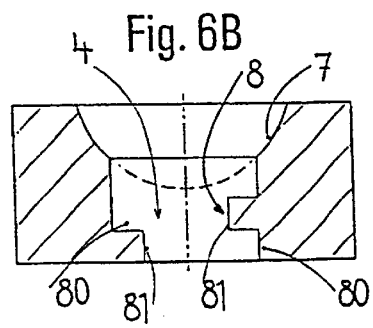
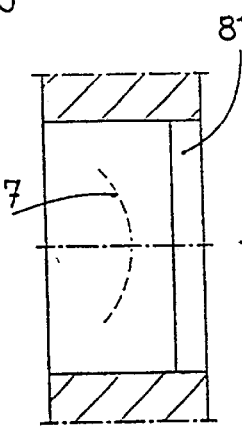
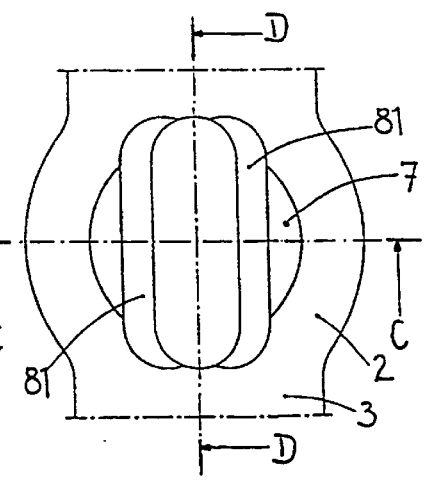
Fig. 6D
Fig. 6B
Fig. 6C
Fig. 6A

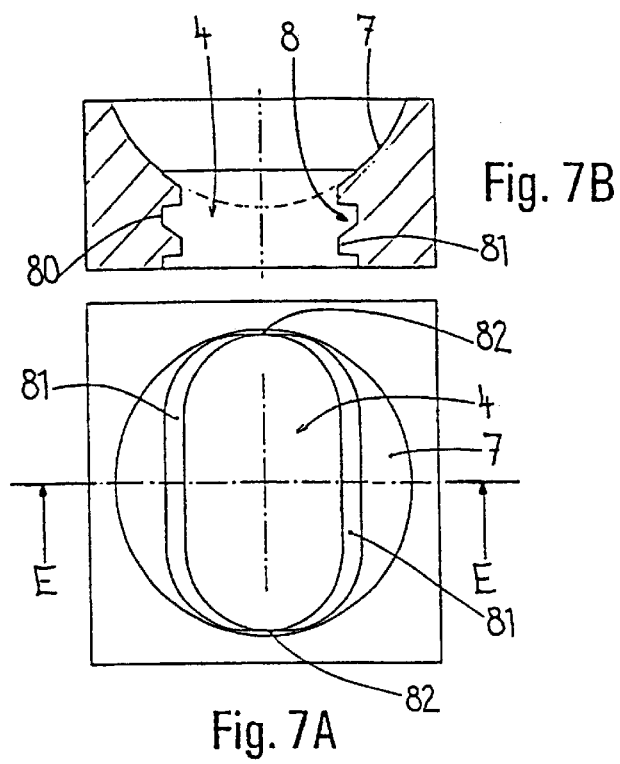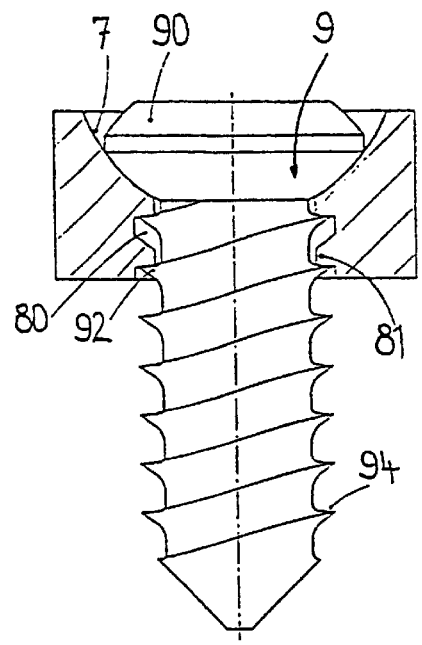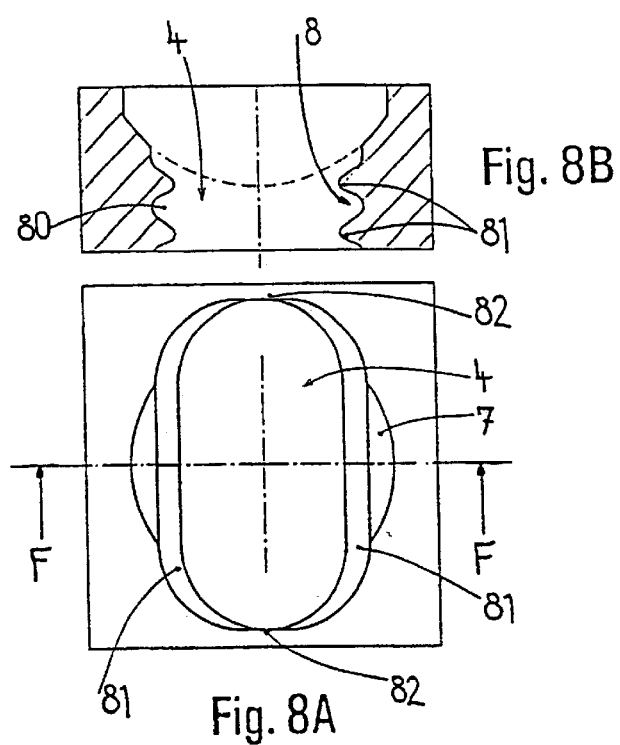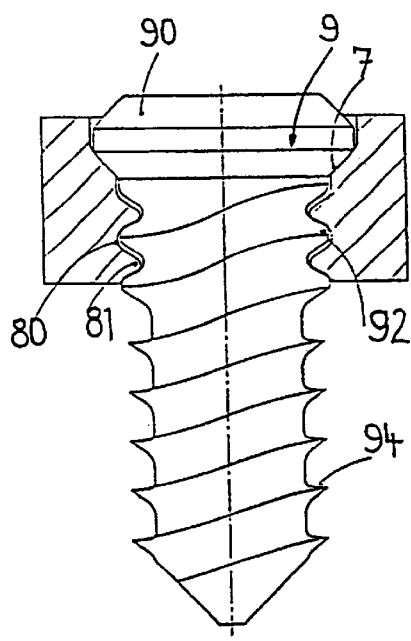

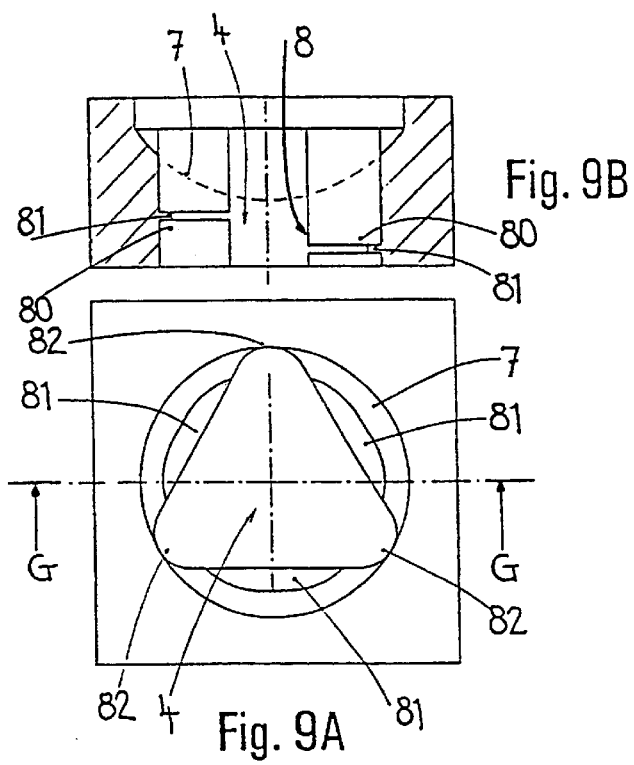
Fig. 9B
Fig. 9A
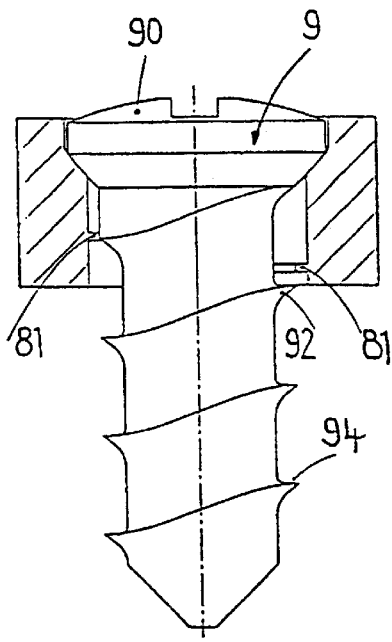
Fig. 9C
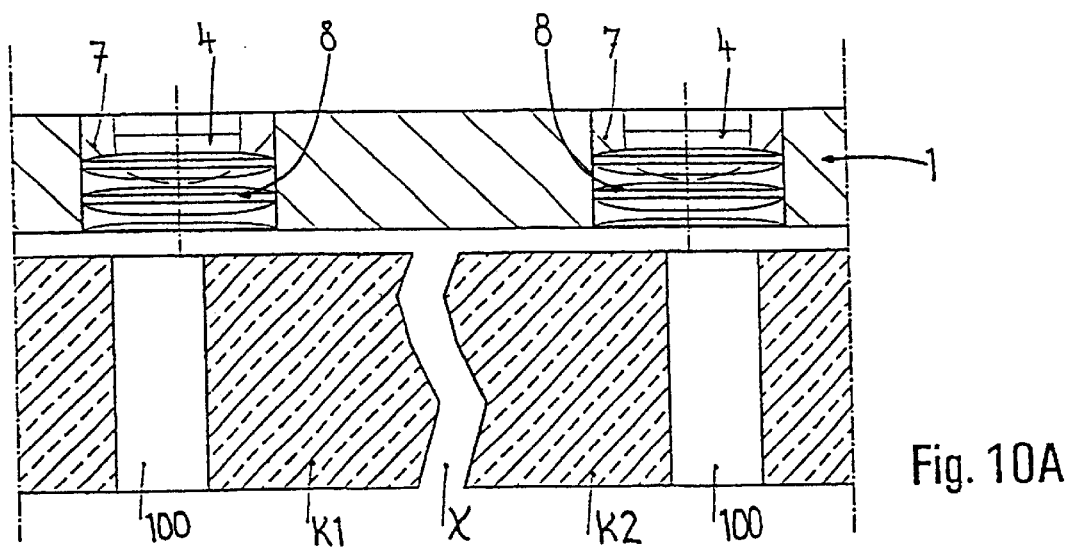
Fig. 10A

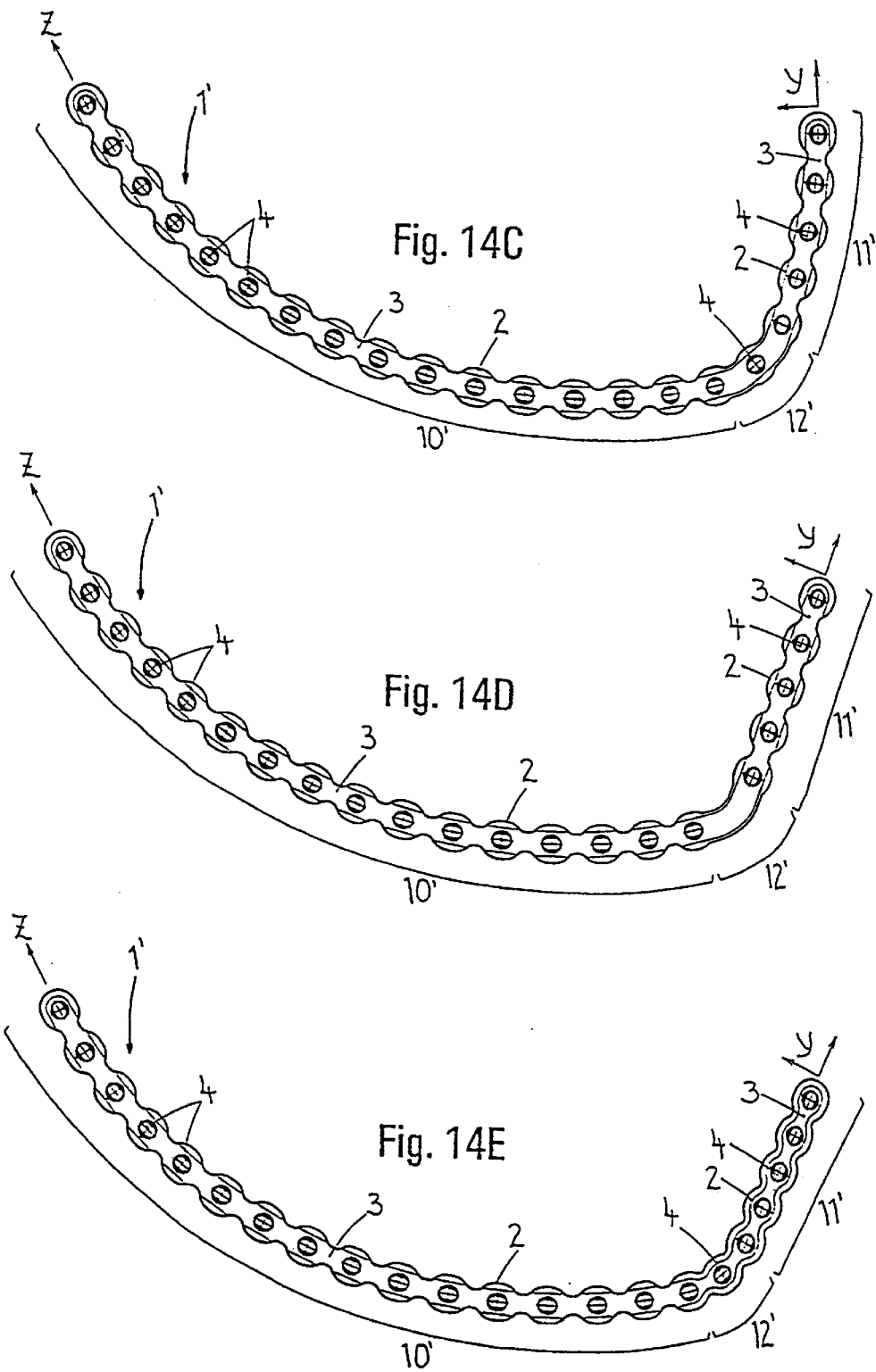

BLOCKABLE BONE PLATE

FIELD OF APPLICATION OF THE INVENTION

The present invention relates to a blockable bone plate with secured bone screws which serve in particular as a reconstruction system for the maxillofacial region of the human skull, for example for the lower jaw. For the time being, the shorter terms "plate", "screw" and "plate-screw connection" are used. Such plates are used, for example, to strengthen weakened and damaged bone structures. In the case of large continuity defects, the plates have to provide stability over long periods of time and take up the loads which the missing bone would have supported. Plates of this type consist in their simplest form of a straight elongate branch with a multiplicity of plate members, in each of which a screw hole is provided for receiving a screw. The plate can be tailored to the required length, which is done by cutting off surplus plate members, and can be bent to adapt it to the local anatomical situation.

The bone plate and a plate-screw connection have to satisfy the following requirements:

high degree of strength and stability of the bone plate;

high degree of rigidity of the plate-screw connection;

flexibility of the plate in all planes with minimal loss of strength both in the plate plane and also around the plate plane, including as torsion;

possibility of applying the various biological tissue types on the plate;

least possible surface pressure of the plate on the periosteum; and securing (so-called blocking) of the screws passing through the plate in order to prevent the screws from coming loose.

PRIOR ART

In order to keep the surface pressure of the plate on the periosteum to a minimum, U.S. Pat. No. 5,810,823 proposes arranging spacer elements with an internal thread which are fixed on or can be fitted onto the lower surface of the plate and which sit on the bone and are passed through by the threaded shanks of the screws. Spacer elements whose position can be varied also permit an orientation of the screws which deviates from the vertical. Although this construction avoids the plate pressing on the periosteum over a large surface area, increased pressure nevertheless arises at the points of contact of the spacer elements. The relatively small spacer elements that can be fitted complicate the surgical procedure. Regardless of whether the spacer elements are fixed or can be fitted in place, they do not provide any improved securing of the screws against their inadvertently coming loose. WO 96/39975 describes a blocked plate-screw connection in which recessed securing elements are provided on the lower surface of the plate, which can be fitted in the area of the screw holes. The threadless neck portion of the screw shank passes through the individual securing element, said screw shank having a smaller diameter than the threaded part. The threaded part can firstly be passed through the securing element and screwed into the bone, the screw head coming to lie in a countersink on the upper surface of the plate. After heat treatment, the securing element shrinks so that the plate is held at a distance from the periosteum and the screw is secured against unscrewing. This system requires the special securing elements and devices and is therefore expensive to manufacture and handle.

The company brochure "SYNTHES®—THORP Reconstruction Set" from STRATEC Medical, Waldenburg, Switzerland, discloses a plate system in which anchoring screws are first screwed through the screw holes of the plate into the bone. An expansion screw is screwed into the slotted head of the anchoring screw which sits in the screw hole. In this way, the head of the anchoring screw presses against the wall of the screw hole in the plate. The anchoring screw is thus secured against unscrewing and the plate is held as it were at a distance from the periosteum. To ensure that the screw holes in the plate do not narrow upon bending, bend inserts are provided as insertable cores. The relatively large number of parts means that the operation takes longer and entails more instrumentation and is as a whole made more difficult.

A further development of a blockable plate-screw connection is known from U.S. Pat. No. 5,709,686. The bone plate has a plurality of holes provided in the direction of the longitudinal axis of the plate and intended for the passage of screws. The screw hole is of oval shape, its main axis lying in the longitudinal axis of the plate. On the upper surface of the plate, the screw hole is surrounded by a spherical countersink. Over the shorter minor axis of the screw hole there is a partial internal thread whose turns each run out to the main axis of the oval screw hole. The internal thread serves to receive a threaded portion which lies under the head of the screw and which in diameter is widened compared to the threaded shank of the screw. The screw hole opens toward the lower surface of the plate in the area of both ends of the main axis, i.e. outside the internal thread on the longitudinal axis of the plate.

In the clinical application of the plate, the threaded shank of the screw protrudes into the bone while the threaded portion with the internal thread engages in the screw hole. The plate is thus supported and is not pressed by the tensile force of the screw onto the periosteum. The screw is secured against inadvertent unscrewing by the threaded connection between the internal thread in the screw hole and the threaded portion of the screw. Plate and screw are blocked. In the event of eccentric application of a screw without threaded portion, the countersink around the screw hole permits a compression between bone compartments. Screws without a threaded portion for blocking can also be screwed in in a direction deviating from the vertical. Greater clearance for this exists in the direction of the longitudinal axis of the plate as a result of the oval hole shape and the only partial internal thread in the screw hole.

The plate-screw connection according to U.S. Pat. No. 5,709,686 permits satisfactory blocking and an additional securing of the screws, but there are still serious disadvantages, for example:

To prevent deformations of the internal thread in the screw holes when bending the plate, bend inserts again have to be used.

Even at low torques when the screw is being screwed in, the internal thread in the screw hole can be overscrewed. With standard screwdrivers, such critical torques can be quite easily applied. A damaged plate is unusable; a new plate has to be used and if appropriate also a new screw.

In a blocked plate-screw connection, the inserted screws can only be positioned vertically, which makes it necessary to use exactly vertical drill guides.

Because of the overall geometry of the plate holes, machining has to be done from two directions, which makes the plate production more expensive.

OBJECT OF THE INVENTION

In view of the stated inadequacies of the blockable bone plates known to date, with secured screws, the object of the invention is to propose an improved blockable plate-screw connection. The aim here in particular is to manage without third parts such as inserts or expansion screws for blocking and bend inserts. The connections are intended to be less sensitive to overscrewing and angled offset of the screws in relation to the vertical and the longitudinal axis of the plate. It is desirable, within the plate-screw connection, to obtain a high release torque for the screws in order thereby to more effectively prevent the screws from coming loose. The clinical application is to be made as straightforward as possible for the operator. It must still be possible to perform osteosynthetic bone compression and to use the connection with conventional screws unblocked. Finally, the parts of the connection must be able to be manufactured economically in serial production.

OVERVIEW OF THE INVENTION

The further development of the blockable bone plate according to the invention is based on a bone plate and screws with a blocking thread according to the generic type from U.S. Pat. No. 5,709,686. The plate consists of a plurality of plate members which are connected to each other via webs. A screw hole is provided in at least some plate members, preferably in each plate member, and is surrounded on the upper surface of the plate by a spherical countersink. Provided internally in the screw hole there is an engagement contour which consists of contour valleys and adjacent remaining contour peaks partially running in a horizontal and radial peripheral direction on the wall of the screw hole. The diameter of the countersink for receiving the screw head is greater than the clear width of the engagement contour. This runs out to the edges of the engagement contour so that smooth uncontoured wall areas are left there in the screw hole. In relation to the threaded shank of the screw, the screw hole is shaped as an oblong hole. The engagement contour is preferably produced by milling and has for example a pointed, round, trapezoidal or serrated configuration.

The screw intended for blocking has, under the screw head, a blocking thread which has the same diameter as or a greater diameter than the thread on the threaded shank which is intended for engagement in the bone. When fixing the plate on the bone, the screw passes through the screw hole with its threaded shank, and the thread of the threaded shank screws into the bone. In the final phase of screwing-in of the screw, the blocking thread under the screw head engages in the engagement contour in the screw hole. As the blocking thread with its helical course and its pitch is not complementary in form to the engagement contour, deformation occurs on both, resulting in a connection resistant to loosening. A blocking of reduced strength can be obtained if on the screw there is a complete thread whose uppermost turns run jammed underneath the engagement contour.

Particular advantages in the osteosynthesis of fractures on curved bones, for example a lower jaw, are obtained using the blocking according to the invention on a bone plate with a plate longitudinal axis in the shape of an arc of a circle. The bone plate consists at least of a main segment in the shape of an arc of a circle. For special purposes, the main segment is provided with a lateral segment which is attached to it at one end or at both ends and lies in the plate plane, and which lateral segment is straight or curved. Some screw holes on the bone plate can be designed not for blocking, but as cylindrical standard screw holes or as oriented compression holes. The bone plate in the shape of an arc of a circle preferably acquires its shape without forming, so that the plates reach the surgeon without initial weakening caused by bending stresses.

By virtue of the invention, a blockable plate-screw connection is now available with the following advantages:

The plate-screw connection is efficient in clinical application since no third parts are needed for blocking. Also, no bend inserts are needed when bending the plate. The plate tends to bend in the area of the webs connecting the individual plate members. However, even in the event of bending within the screw hole, the function of the blocking is not impaired.

During blocking, no forces act on the periosteum, so that the latter is protected. The plate can be positioned at a distance from the bone similar to a fixator.

The internal engagement contour in the screw hole also permits a slight angular offset of the inserted screw in relation to the vertical and to the longitudinal axis of the plate. This is achieved without any functional loss of the blocking.

Upon generation of compression, the screws are not subjected to tensile stress since the blocking of the screw in the plate prevents any axial movement between plate and bone.

The inserted screws are better protected against inadvertent loosening because a high release torque has to be applied. This is due to the deformations during blocking on the internal engagement contour on the screw hole and on the associated thread of the screw.

The risk of overscrewing and thus of damage to the plate is reduced. In conventional plates, the screws are overscrewed even at low insertion torques which can be applied effortlessly with standard screwdrivers.

The engagement contour arranged internally in the screw holes causes substantially less notch effect than a conventional internal thread, as a result of which there is less risk of the plate breaking.

The plate can be fitted with different screws, namely those with which blocking is obtained and those without blocking. In the latter case, the screw holes function as neutral compression holes for receiving the screw head. This, for example, for applying small screws in order to fasten a bone compartment. Here, the screw can also be inserted at an inclination.

Since the complete geometry of the screw holes in the plate can be worked from one side, retooling is not required during machining, thus resulting in overall cost-effective production which can also be executed with precision at a reasonable cost.

In the configuration of the bone plate with a longitudinal axis of the plate in the shape of an arc of a circle (at least in the main segment if the bone plate is provided with a lateral segment attached at one end or both ends), after bending the webs out of the plate plane, as it were over the surface, it is possible to adapt the bone plate closely to the bone. The additional bending in the plate plane is dispensed with, that is to say the setting or twisting over the edge. By means of the circular arc-shaped starting geometry, the bone plate assumes the inclination of a circular section of the jacket surface of a cone. This reduces the surgical effort when adapting the plate and also reduces the losses of strength thereof because of minimal deformation. There is ideal adaptation of the bone plate in its longitudinal extent and the inclination over the plate width.

BRIEF DESCRIPTION OF THE ATTACHED DRAWINGS

In the drawings:

FIG. 1A shows a bone plate screwed onto a fractured lower jaw;

FIG. 1B shows a bone plate screwed onto the lower jaw for bridging a continuity defect;

FIG. 2A shows a plan view of a bone plate with uniformly oriented screw holes;

FIG. 2B shows the representation according to FIG. 2A, with differently oriented screw holes;

FIG. 4A shows the bone screw according to FIG. 3A screwed vertically into and blocked in a screw hole from FIG. 2E;

FIG. 4B shows the view according to FIG. 4A, with the inserted bone screw blocked at an inclination;

FIG. 4C shows bone screws according to FIG. 3A screwed into and blocked in screw holes with engagement contours in a first embodiment according to FIG. 2E of a curved bone plate;

FIG. 4D shows bone screws screwed into a curved and twisted bone plate according to FIG. 2A;

FIG. 5A shows the bone screw according to FIG. 3A with blocking thread, deformed after blocking;

FIG. 5B shows a screw hole with an engagement contour in a first embodiment from FIG. 2E, deformed after blocking;

FIG. 6A shows a plan view of a screw hole with an engagement contour in a second embodiment;

FIG. 6B shows the view according to FIG. 6A as a section along the line C—C;

FIG. 6C shows the view according to FIG. 6A as a section along the line D—D;

FIG. 6D shows the bone screw according to FIG. 3E, screwed into and blocked in the screw hole from FIG. 6B;

FIG. 7A shows a plan view of a screw hole with an engagement contour in a third embodiment;

FIG. 7B shows the view according to FIG. 7A as a section along the line E—E;

FIG. 7C shows the bone screw according to FIG. 3F, screwed into and blocked in the screw hole from FIG. 7B;

FIG. 8A shows a plan view of a screw hole with an engagement contour in a fourth embodiment;

FIG. 8B shows the view according to FIG. 8A as a section along the line F—F;

FIG. 8C shows the bone screw according to FIG. 3G, screwed into and blocked in the screw hole from FIG. 8B;

FIG. 9A shows a plan view of a screw hole with an engagement contour in a fifth embodiment;

FIG. 9B shows the view according to FIG. 9A as a section along the line G—G;

FIG. 9C shows the bone screw according to FIG. 3H, screwed into and blocked in the screw hole from FIG. 9B;

FIG. 10A shows the situation before closure of a fracture by means of compression osteosynthesis;

FIG. 14C shows the bone plate according to FIG. 14B with an additional screw hole in the strengthened angle area;

FIG. 14D shows the bone plate according to FIG. 14A without an additional screw hole in the strengthened angle area; and FIG. 14E shows the bone plate according to FIG. 14A with a reduced spacing of the screw holes in the lateral segment.

ILLUSTRATIVE EMBODIMENTS

Figure 2C:
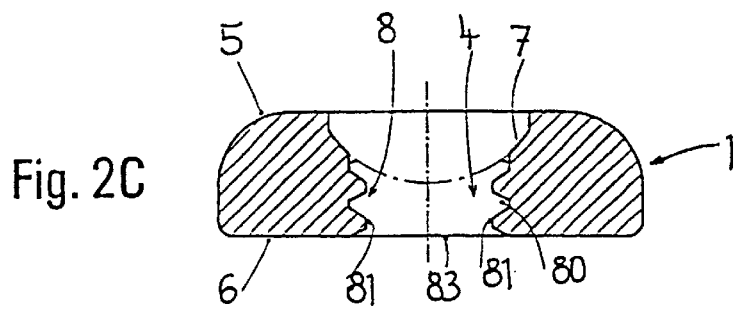
FIG. 2C shows the bone plate according to FIG. 2A in the section along the line A—A, with the engagement contour in a first embodiment, outline sketch.
Figure 2D:
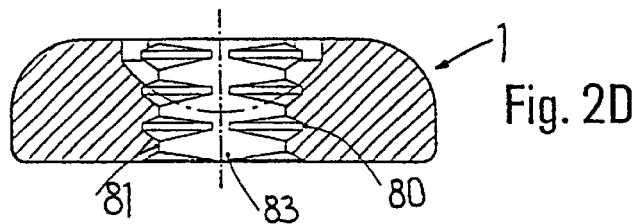
FIG. 2D shows the representation according to FIG. 2C with the engagement contour, actual contour.
Figure 2E:
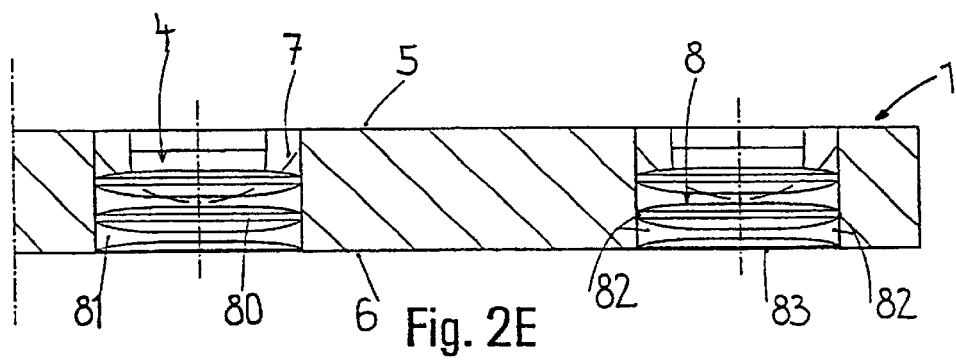
FIG. 2E shows the bone plate according to FIG. 2A in the section along the line B—B.

Referring to the attached drawings, there now follows a detailed description of illustrative embodiments of the osteosynthetic bone plate according to the invention with blockable bone screws.

The following observation applies to the whole of the description given below. If, for the purposes of clarity of the drawings, reference numbers are included in a figure but are not mentioned in the directly associated text of the description, reference is made to their mention in preceding or subsequent figure descriptions. In the interests of clarity, repeated mention of components in subsequent figures is for the most part avoided provided that it is clear from the drawings that these are "recurring" components.

FIGS. 1A and 1B

These figures show two typical applications of the blockable bone plate 1 according to the invention which, together with bone screws 9, constitutes a plate-screw connection. First, the plate 1 is eminently suitable for osteosynthesis of a lower jaw which has fractured into bone compartments (see FIG. 1A). A further principal use lies in the bridging of a continuity defect, that is to say, where a bone section is missing, the plate 1 has to take up the load permanently and stabilize the lower jaw (see FIG. 1B). Pressing of the plate 1 on the periosteum and inadvertent loosening of the inserted screws are to be avoided, so that a solid blocking is particularly relevant here.

FIGS. 2A to 2E

In its simplest form, the plate 1 is an elongate linear branch through which the longitudinal axis Z of the plate extends. The plate 1 is made up of a multiplicity of plate members 2 which are connected to each other via webs 3. The webs 3 form waist-like transitions between adjacent plate members. A screw hole 4 is provided in at least some plate members 2, but preferably in each plate member. On the upper surface 5 of the plate, the screw holes 4, which open out on the lower surface 6, are surrounded by a spherical countersink 7. Located inside the screw hole 4 there is an engagement contour 8.

The engagement contour 8 looks like a partial thread, but only at first sight; in fact the engagement contour 8 consists of contour valleys 80 and alternating adjacent contour peaks 81 arranged on the wall of the screw hole 4 and extending parallel to the plate plane Y. The contour valleys 80 and peaks 81 run partially in the peripheral direction in the screw hole 4, i.e. run out to the edges of the engagement contour 8, so that uncontoured wall areas 82 are left there in the screw hole 4. The countersink 7 has a depth which is such that the screw heads are received in a recessed manner. The diameter of the countersink 7 is greater than the clear width of the engagement contour 8. The distance between opposite contour valleys 80 and contour peaks 81 is smaller than the distance between the opposite uncontoured wall areas 82, so that the exit 83 of the screw hole 4 on the lower surface 6 of the plate has an oblong hole shape. The contour valleys 80 and contour peaks 81 forming an engagement contour 8 can be arranged substantially parallel to the longitudinal axis Z of the plate or at an angle thereto, so that the longitudinal dimension of the exit 83 lies on the longitudinal axis Z of the plate (see FIG. 2A) or assumes different angles to the longitudinal axis Z of the plate (see FIG. 2B). Correspondingly, the uncontoured wall areas 82 are distributed along the longitudinal axis Z of the plate or are offset thereto. In this first embodiment of the engagement contour 8, the contour valleys 80 and contour peaks 81 form trapezoidal threads.

FIG. 3A

At its top, the bone screw 9 has the screw head 90 which underneath is designed as a spherical cap to complement the countersink 7 in the plate 1. Located in the screw head 90 there is a recess 91, for example a cross slot, into which a screwing instrument can be inserted from above. Located under the screw head 90 there is a blocking thread 92, designed here as a trapezoidal thread, corresponding to the engagement contour 8. The double-threaded bone thread 94 is arranged along the screw shank 93. The bone thread 94 has, for example, an external diameter of 2.5 mm, while the external diameter of the blocking thread 92 is significantly greater, for example 3.2 mm.

FIG. 3B

If the diameter, for example 2.5 mm, of the bone thread 94 in the preceding screw 9 is too small, because the screw hole drilled in the bone is too large or the strength is not sufficient, it is possible to use a modified screw 9 with a greater diameter of the bone thread 94, for example 3.2 mm. Even with this diameter, the bone thread 94 can be moved effortlessly through the engagement contour 8 in the plate 1. By contrast, the wide trapezoidal flanks of the blocking thread 92 result in a blocking with the engagement contour 8.

Figure 3A:
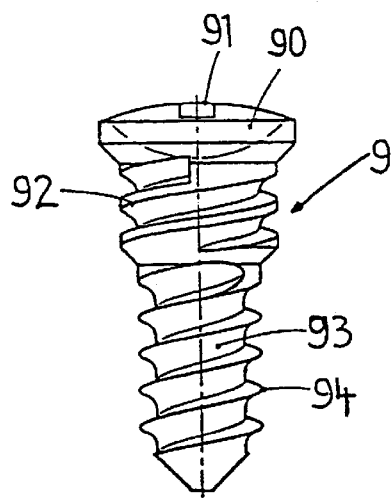
FIG. 3A shows a double-threaded bone screw with blocking thread in the neck area.
Figure 3B:
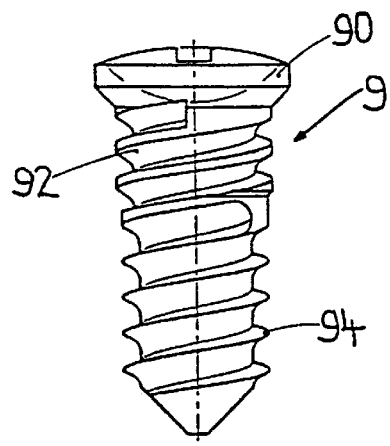
FIG. 3B shows the double-threaded bone screw according to FIG. 3A with blocking thread in the neck area and thicker screw shank.
Figure 3C:
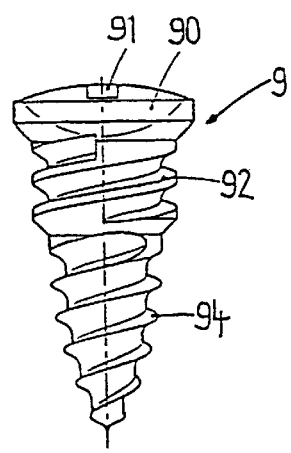
FIG. 3C shows a bone screw with blocking thread in the neck area and self-boring and self-tapping thread on the screw shank.
Figure 3D:
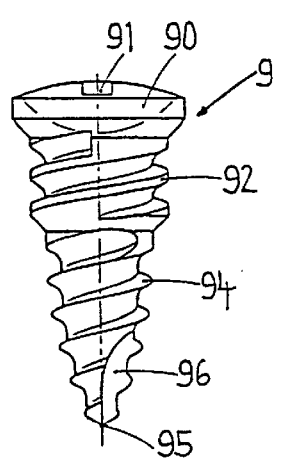
FIG. 3D shows the bone screw according to FIG. 3C with blocking thread in the neck area and self-boring and self-tapping thread on the screw shank and additional cutting groove.

FIGS. 3C and 3D

For a blockable plate-screw connection, it is possible as an alternative to use the self-boring screw 9 shown which likewise has, under the screw head 90, a trapezoidal blocking thread 92 from which the bone thread 94 extends. By way of example, the bone thread 94 has a maximum external diameter of 2.5 mm and the blocking thread 92 has an external diameter of 3.2 mm. The screw 9 according to FIG. 3D is additionally provided with a cutting groove 96 at the tip 95 of the shank.

Figure 3E:
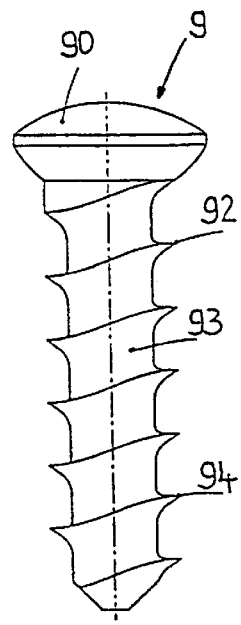
FIG. 3E shows a single-threaded self-tapping bone screw with pointed thread flanks.
Figure 3F:
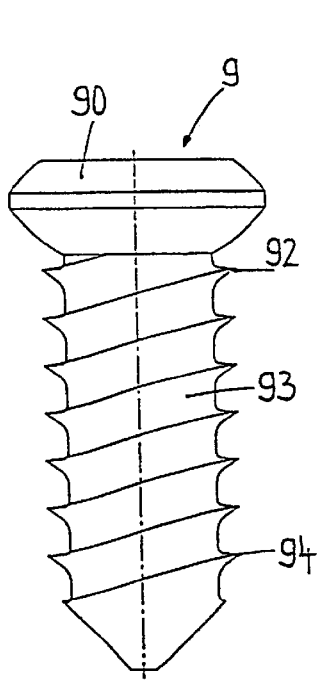
FIG. 3F shows a double-threaded self-tapping bone screw with pointed thread flanks and thicker screw shank.
Figure 3G:
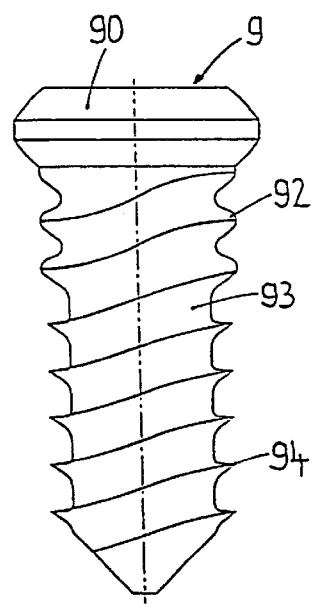
FIG. 3G shows the double-threaded self-tapping bone screw according to FIG. 3F with rounded thread in the neck area.
Figure 3H:
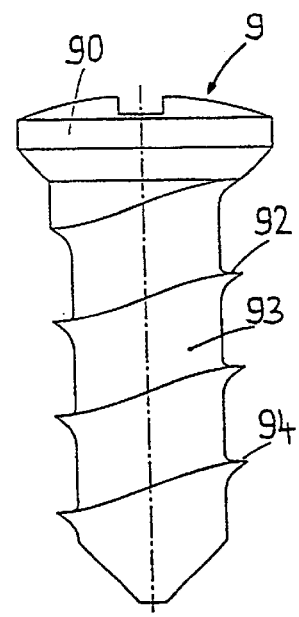
FIG. 3H shows the single-threaded self-tapping bone screw according to FIG. 3E with pointed thread flanks, greater pitch and greater external diameter on the screw shank.

FIGS. 3E, 3F and 3H

These screws 9 have a continuously uniform thread along the screw shank 93, with pointed thread flanks, which thread engages with the suitably contoured engagement contours 8 in the plates 1, in the upper part as blocking thread 92 and in the lower part as bone thread 94. The screws 9 according to FIGS. 3E and 3H are single-threaded, and the screw 9 according to FIG. 3F is double-threaded.

FIG. 3G

This shows a double-threaded screw 9 with rounded thread flanks on the blocking thread 92 and pointed thread flanks on the bone thread 94.

FIGS. 4A to 4D

The engagement contour 8 in the plate 1 allows the screw 9 with the blocking thread 92 to be inserted into the screw hole 4 both vertically (see FIG. 4A) and also at an angle a in relation to the longitudinal axis Z of the plate (see FIG. 4B). Even with the screw 9 positioned at an inclination, fully effective blocking is still achieved; the blocking thread 92 likewise engages in the engagement contour 8. The uncontoured wall areas 82 lying at the ends of the engagement contour 8, with the longitudinal dimension of the exit 83, offer clearance for the approach of the inclined blocking thread 92. By means of the inclined position of the screw 9, the screw head 90 comes to lie obliquely in the countersink 7. The in practice complete and seamless bearing of the screw head 90 in the countersink 7 results from the complementary spherical surfaces lying on each other.

Bending the plate 1 about the plate plane Y (see FIG. 4C) or in the plate plane Y or twisting the plate 1 (see FIG. 4D) does not adversely affect the function of the blocking. On the one hand, the main change in the shape of the plate 1 takes place in the area of the webs 3, and on the other hand the engagement contour 8, as a result of limited deformation, does not lose any of its effectiveness.

FIGS. 5A and 5B

These show the deformation which is caused during blocking between the engagement contour 8 and the blocking thread 92 inserted into the latter, which deformation secures the screw 9 in a very effective manner against inadvertently coming loose. Engagement contour 8 and blocking thread 92 are not complementary to each other. The blocking thread 92 has a helically extending thread tooth; or correspondingly, in the case of a double-threaded thread, two teeth. The engagement contour 8 by contrast consists of the contour valleys 80 and contour peaks 81 which do not extend in a pitch angle, as in the case of a helical thread. When the blocking thread 92 is inserted between the contour peaks 81, there is a deliberate collision and mutual deformation. The blocking thread 92 requires as a supplement helical internal thread turns, and the horizontally extending contour peaks 81 brace themselves against the insertion of the blocking thread 92. By means of this contrast the blocking thread 92 and the engagement contour 8 deform, i.e. both develop bend edges 920, 810 which are directed toward each other and which abut each other when the screw 9 is unscrewed and thus form a considerable resistance to inadvertent loosening. If the screw 9 is to be unscrewed, a high torque has to be exerted to achieve a partial return to shape of the bend edges 920, 810 and to overcome the increased frictional resistance. For the engagement contour 8, the preferred range of the vertical distance between recurring structures—the contour valleys 80 or the contour peaks 81—is between 0.5 mm and 1.0 mm. The contour valleys 80 can expediently be produced by milling, so that the contour peaks 81 remain between the milled contour valleys 80.

FIGS. 6A to 6D

The second embodiment of the engagement contour 8 is likewise made up of contour valleys 80 and contour peaks 81 which are worked into the wall of the screw hole 4, parallel to the longitudinal axis Z of the plate, and run out at their ends in uncontoured wall areas 82. The particular feature here lies in the fact that contour valleys 80 and contour peaks 81 lie offset in relation to each other on both sides of the longitudinal axis Z of the plate. In this way the uniform thread on the screw shank 93 acts in the upper part as a blocking thread 92, whose thread teeth engage behind the contour peaks 81, while the lower part acts as a bone thread 94 for insertion into the bone. The screw head 90 with its spherical cap bottom sits in the spherical countersink 7.

FIGS. 7A to 7C

The third embodiment of the engagement contour 8 is made up of contour valleys 80 and contour peaks 81 which extend inside the screw hole 4 parallel to the longitudinal axis Z of the plate and are serrated in shape. Here, the contour valleys 80 and contour peaks 81 lie at the same height on both sides of the longitudinal axis Z of the plate and, at the ends of the engagement contour 8, run out in uncontoured wall areas 82. The double-threaded screw 9 also used in this plate-screw connection has a uniform thread along its screw shank 93, the upper part of which engages as a blocking thread 92 under the contour peaks 81, while its lower part is provided as a bone thread 94 for insertion into the bone. The screw head 90 is again recessed in the spherical countersink 7.

FIGS. 8A to 8C

In this fourth embodiment of the engagement contour 8, the contour valleys 80 and the contour peaks 81 have a rounded shape. Complementing the rounded shape of the engagement contour 8, use is made of a screw 9 with a double-threaded blocking thread 92 which is designed as a rounded thread. The pointed double-threaded bone thread 94 extends below the blocking thread 92. The rounded contour valleys 80 and contour peaks 81 lie at the same height on both sides of the longitudinal axis Z of the plate, with uncontoured wall areas 82 at the ends of the engagement contour 8. The blocking thread 92 assumes a blocked engagement with the contour valleys 80 and peaks 81. The screw head 90 is accommodated in the countersink 7.

FIGS. 9A to 9C

The particular feature of the fifth embodiment of the engagement contour 8 lies in the fact that the contour peaks 81 in the screw hole 4 are offset in relation to each other in the plate plane Y by in each case 120° and in height—relative to the plate plane Y—lie in a stairway configuration with respect to one another. Contour valleys and peaks 80, 81 have an angular shape. Corresponding to the engagement contour 8, the screw 9 used has a uniform thread running along its screw shank 93, the upper part engaging as a blocking thread 92 under the contour peaks 81, and the lower part forming the bone thread 94. The spherical countersink 7 accommodates the screw head 90.

Figure 10B:
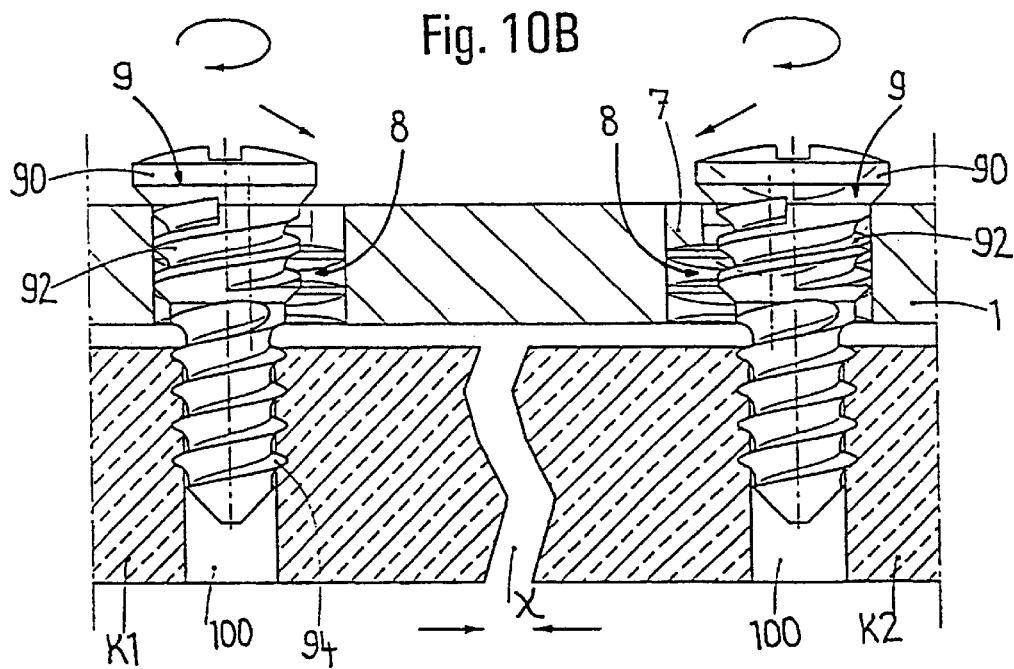
FIG. 10B shows the situation during closure of the fracture.
Figure 10C:
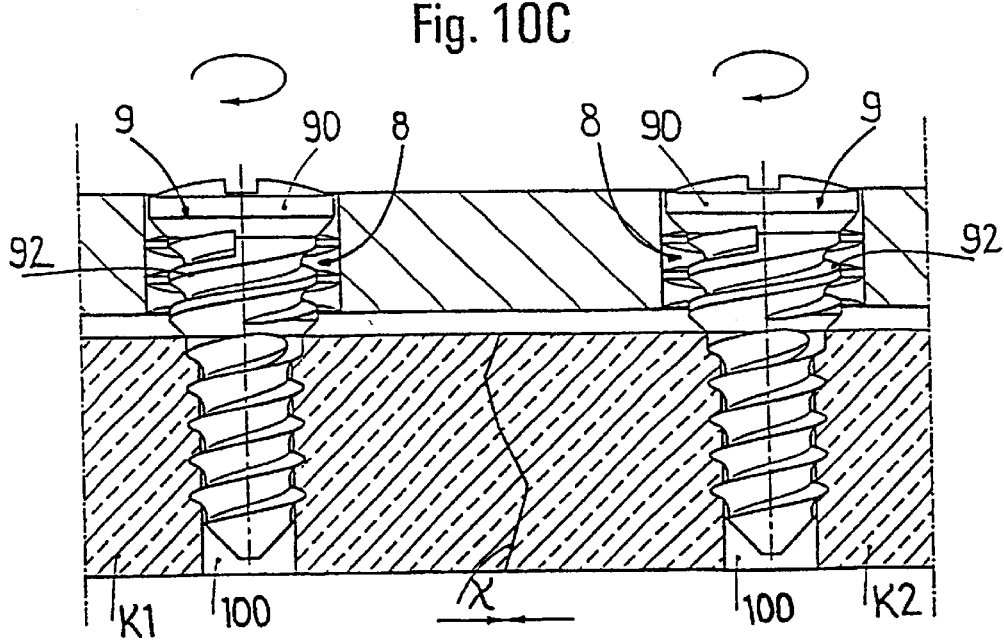
FIG. 10C shows the situation after closure of the fracture.
Figure 11A:
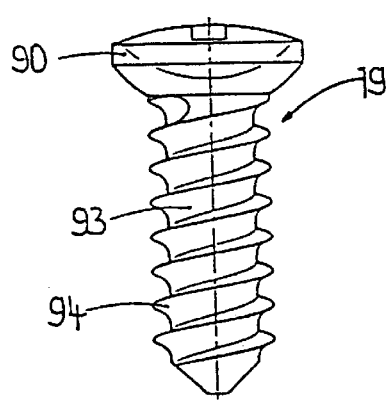
FIG. 11A shows a bone screw without blocking thread.
Figure 11B:
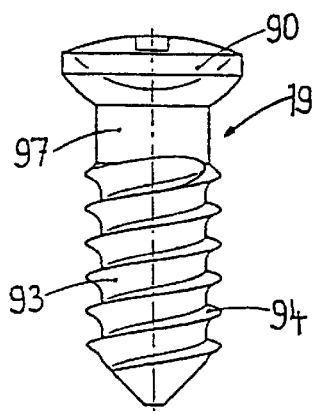
FIG. 11B shows the bone screw without blocking thread according to FIG. 11A, with thicker screw shank.
Figure 11C:
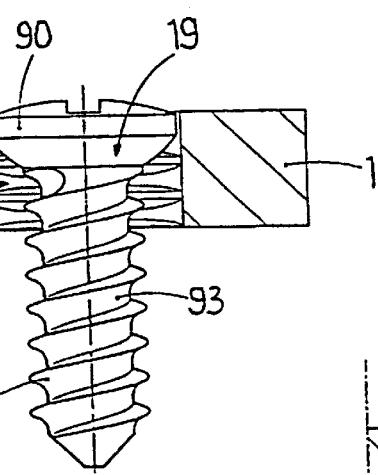
FIG. 11C shows the bone screw according to FIG. 11A screwed vertically into a screw hole from FIG. 2E, and not blocked.
Figure 11D:
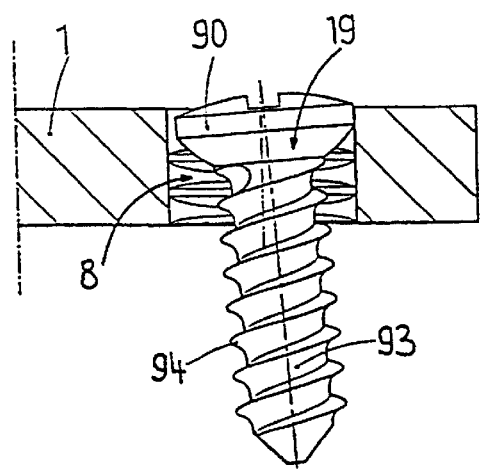
FIG. 11D shows the view according to FIG. 11C with the bone screw screwed in at an inclination and not blocked.
Figure 11E:
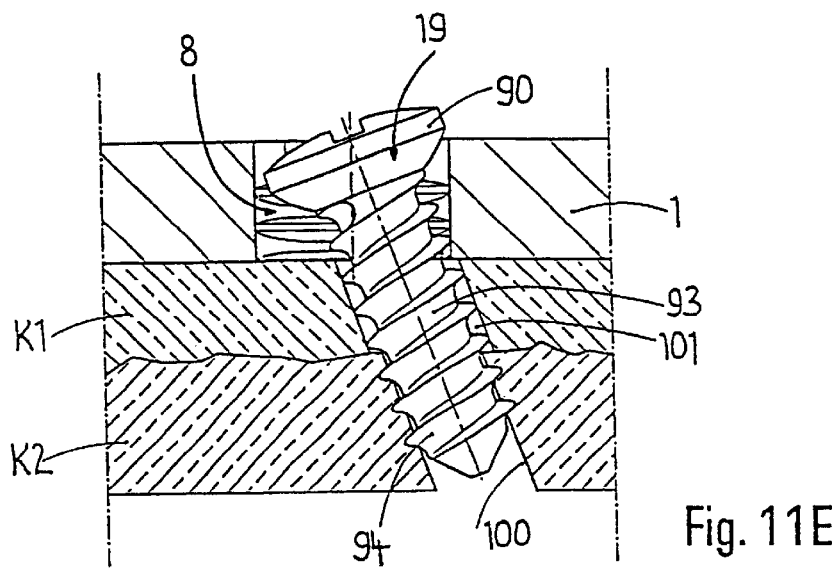
FIG. 11E shows the situation in traction screw osteosynthesis, with a bone screw without blocking thread according to FIG. 11A screwed into a screw hole with engagement contours in a first embodiment according to FIG. 2E, and not blocked.

FIGS. 10A to 10C

The clinical application of the plate-screw connection is illustrated using the example of compression osteosynthesis. In the starting situation (see FIG. 10A), that is to say before closing the fracture, bores 100 are formed in the two bone compartments K1, K2 to be connected, said bores being eccentric in relation to the screw holes 4 in the plate 1. The distance between the bores 100 is greater than the distance between the screw holes 4 in the plate 1, which is positioned over the fracure site with the bone gap X. The screw holes 4 have the engagement contours 8 and countersinks 7.

To close the fracture (see FIG. 10B), screws 9 are introduced through the screw holes 4 of the plate 1 and into the bores 100. With the screw heads 90 still protruding, the screws 9 are at first eccentric in the screw holes 4. As the screws 9 are screwed in further, the bone thread 94 penetrates deeper into the bores 100 and the spherical surfaces under the screw head 90, interacting with the spherical countersinks 7 in the screw holes 4, effect the successive centering of the screws 9. At the same time the blocking thread 92 of the screws 9 begins to engage in the engagement contour 8. Upon centering of the screws 9, these are moved toward each other and in so doing entrain the bone compartments K1, K2 with them; the bone gap X begins to close.

In the final position (see FIG. 10C), the screw heads 90 are recessed to the maximum extent in the countersinks 7 and the screws 9 are centered to such an extent that the bone gap X has completely closed. The bone compartments K1, K2 are now pressed against each other. The blocking is produced between the blocking thread 92 of the screws 9 and the engagement contours 8; the screws 9 are thus secured against coming loose.

FIGS. 11A to 11D

The two screws 19 shown (see FIGS. 11A and 11B) have no blocking thread 92. The screw 19 from FIG. 11A, for example with an external thread diameter of 2.5 mm, is too weak to come into blocking engagement with the engagement contour 8. In the screw 19 from FIG. 11B with a greater external thread diameter, for example 3.0 mm, an undercutting 97 is provided below the screw head 90 so that here once again there is no blocking thread 92. These screws 19 without blocking thread 92, in other words only with the bone thread 94, can likewise be used together with the plate 1 which has engagement contours 8 in its screw holes. Blocking does not take place here (see FIG. 11C), as may be desired in actual use. The screw 19 without blocking thread 92 can also be easily used, inserted at an inclination, together with the plate 1 (see FIG. 11D).

FIG. 11E

This view shows a traction screw osteosynthesis with the plate 1 according to the invention and with a conventional screw 19 without blocking thread 92. The screw head 90 is supported obliquely in the screw hole 4, and the screw shank 93 penetrates the two bone compartments K1, K2 which are to be pressed against each other. In the upper bone compartment K1 there is a through-bore 101 of such width that the bone thread 94 cannot engage. In the lower bone compartment K2 there is a bore 100 of reduced diameter in which the bone thread 94 engages. As the screw 19 is screwed in, the lower bone compartment K2 is drawn against the upper bone compartment k1. The engagement contour 8 does not function here; the thin screw shank 93 passes through said engagement contour 8 without blocking.

Figure 12A:
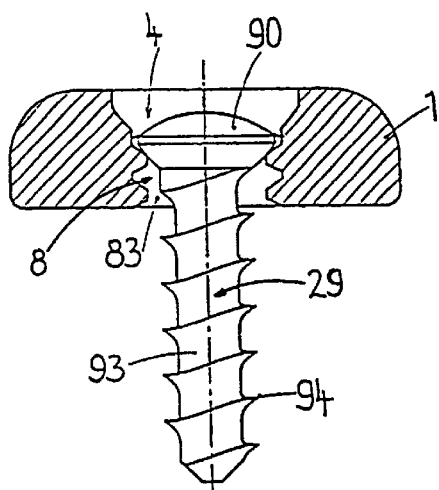
FIG. 12A shows the bone screw according to FIG. 3E screwed vertically into a screw hole from FIG. 2C, and not blocked.
Figure 12B:
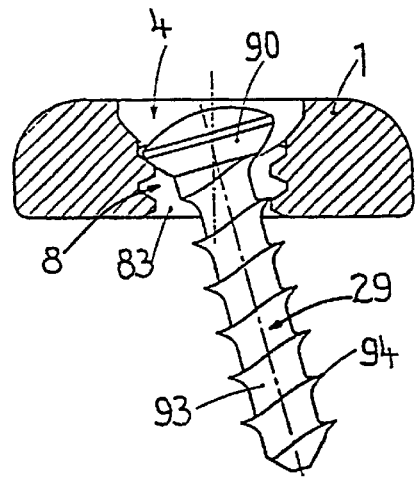
FIG. 12B shows the view according to FIG. 12A with the bone screw screwed in at an inclination, and not blocked.

FIGS. 12A and 12B

For the sake of completeness, these two figures are intended to illustrate that small-fragment screws 29, for example with an external thread diameter of 2.0 mm, can also be inserted into the plate 1 vertically or at an inclination. The small screw head 90 lies deep in the screw hole 4, and the engagement contour 8 remains without function. Such small-fragment screws 29 with a screw shank 93 protruding from the exit 83 and with the bone thread 94 are used for fixing smaller bone fragments.

Figure 13A:
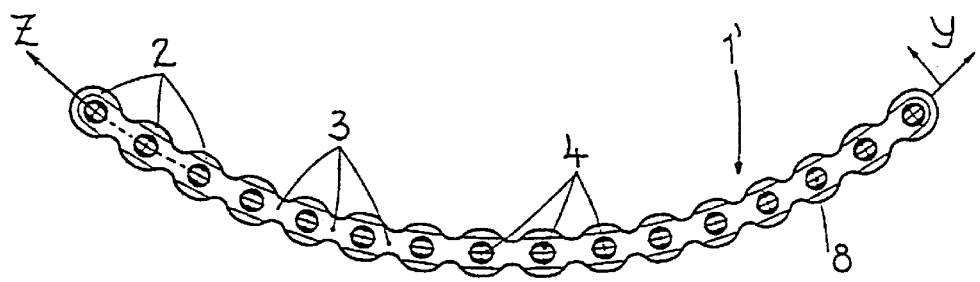
FIG. 13A shows a bone plate with a longitudinal plate axis Z in the shape of an arc of a circle and with 16 screw holes.
Figure 13C:
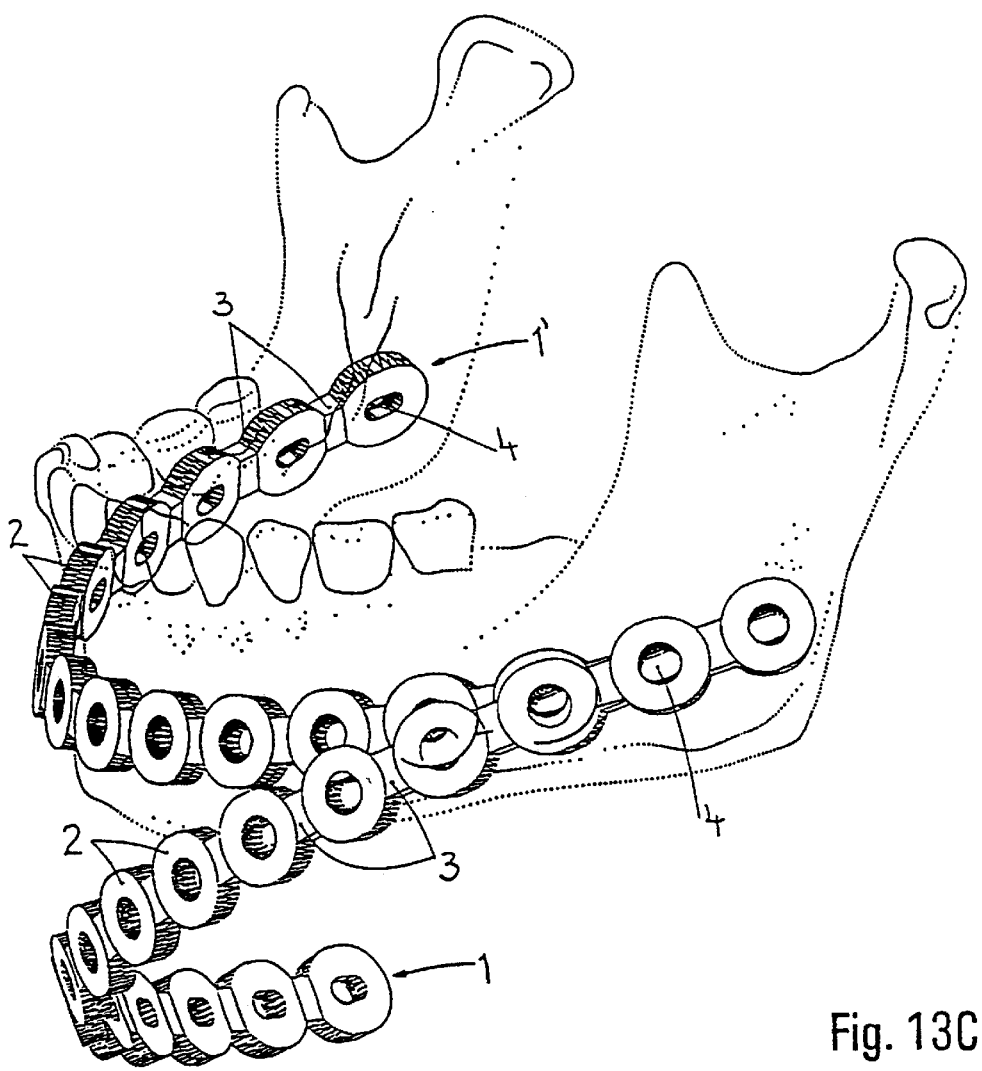
FIG. 13C shows an outline sketch of a human lower jaw with the fitted circular arc-shaped bone plate according to FIG. 13A and with a straight bone plate according to FIG. 2A drifting away from the lower jaw.
Figure 13B:
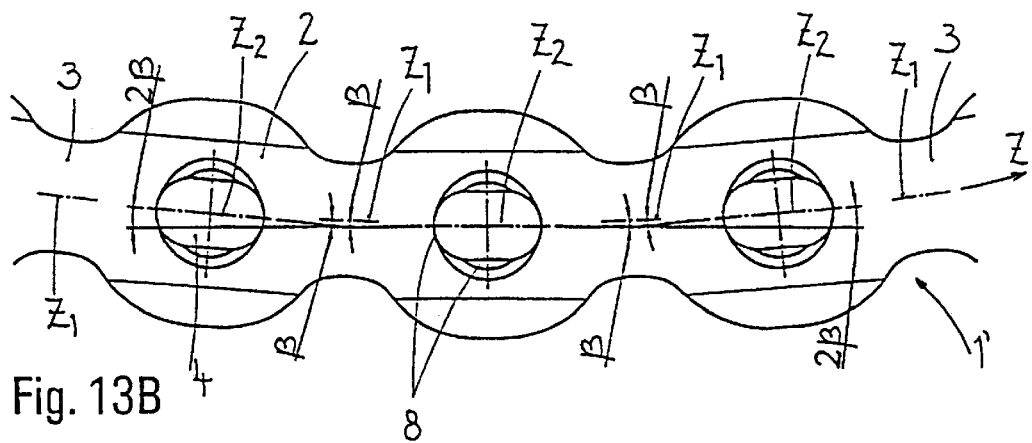
FIG. 13B shows an enlarged view of three plate members according to FIG. 13A.

FIGS. 13A and 13B

This bone plate 1' has a longitudinal axis Z in the shape of an arc of a circle, with a multiplicity of plate members 2 which are connected to each other via webs 3. The plate 1' extends in the unbent starting condition in the plate plane Y. A screw hole 4, with the above-described special engagement contour 8 for blocking, is provided in each of the plate members 2. The circular arc-shape of the longitudinal axis Z of the plate means that between the center axes $Z_1$ of the webs 3 and the center axis $Z_2$ of the respectively adjacent screw hole 4 there is an offset β, for example with $1° \leq \beta \leq 10°$ and preferably β=2.50°. Between two adjacent screw holes 4 there is an offset of 2β, for example with $2° \leq \beta \leq 20°$ and preferably β=5°. It is not imperative that all screw holes 4 have the engagement contour 8 for blocking.

Cylindrical standard screw holes or oriented compression holes can also be present on the plate 1' The circular arc-shaped plate 1' preferably acquires its shape without forming. Depending on the intended use, the plate 1' is produced in the required length, or it is brought to the desired length by cutting off plate members 2 and webs 3. Likewise, the number, positioning, spacing and type of screw holes 4 can be chosen according to the intended use.

FIG. 13C

This figure illustrates in an outline sketch the direction of extent and the geometric adaptation of a plate 1 with a straight longitudinal axis Z and of a plate 1' with a circular arc-shaped longitudinal axis Z, where both plates 1, 1' are applied to a human lower jaw and, in the final bent state, enclosing the lower jaw, extend between the ascending jaw branches.

The straight plate 1 applied to the left jaw branch drifts, after bending the webs 3 out of the plate plane Y, that is over the surface, away from the lower jaw. So that this plate 1 encloses the lower jaw, an additional bending must be carried out in the plate plane Y in each web 3—that is over the edge. Only after this does the plate 1 follow the course of the lower jaw. Since the latter in principle has no vertical surfaces, but extends forward apically, subsequent setting or twisting of the plate members 2 is necessary in order to correctly adapt the plate 1 to the jaw bone.

The plate 1' is more favorably adapted to the jaw bone as the longitudinal axis Z of the plate extends in the shape of an arc of a circle. The plate 1' need only be bent at the webs 3 out of the plate plane Y, that is over the surface, in order to bring the plate into the U-shape enclosing the lower jaw. The bending generally takes place principally in the area of the webs 3. The additional bending in the plate plane Y, that is over the edge, and the setting and twisting are dispensed with here.

Because of the starting geometry in the shape of an arc of a circle, the plate 1', after bending from the plate plane Y, assumes the inclination of a circular portion of the jacket surface of a cone. In this way, both the in principle horizontal U-shaped enclosing of the lower jaw in the longitudinal extent of the plate 1' and also the close adaptation of the plate 1' over its width to the apically extending bone are realized. The starting geometry in the shape of an arc of a circle greatly reduces the surgical work for adapting the plate 1', the plate 1' adapts ideally to the lower jaw, and the losses in strength are reduced because of the minimal deformation, only out of the plate plane Y. The positive effects are obtained particularly if the circular arc-shaped plate 1' is produced without forming, so that the plates 1' reach the surgeon in the curved geometry but without prior bending.

FIGS. 14A to 14E

Figure 14A:
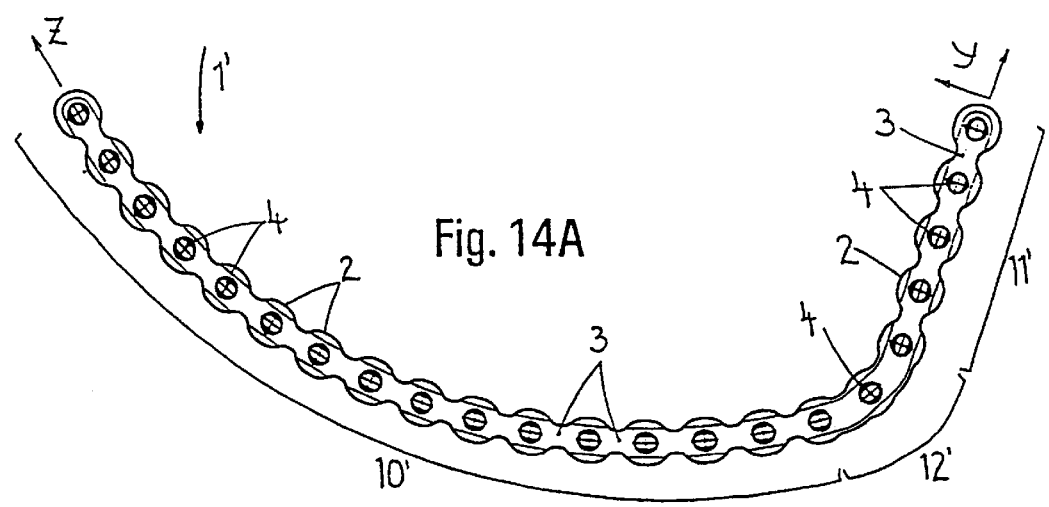
FIG. 14A shows a bone plate for the left branch of the jaw, with a circular arc-shaped main segment according to FIG. 13A, a straight ascending lateral segment, and a strengthened angle area with an additional screw hole.
Figure 14B:
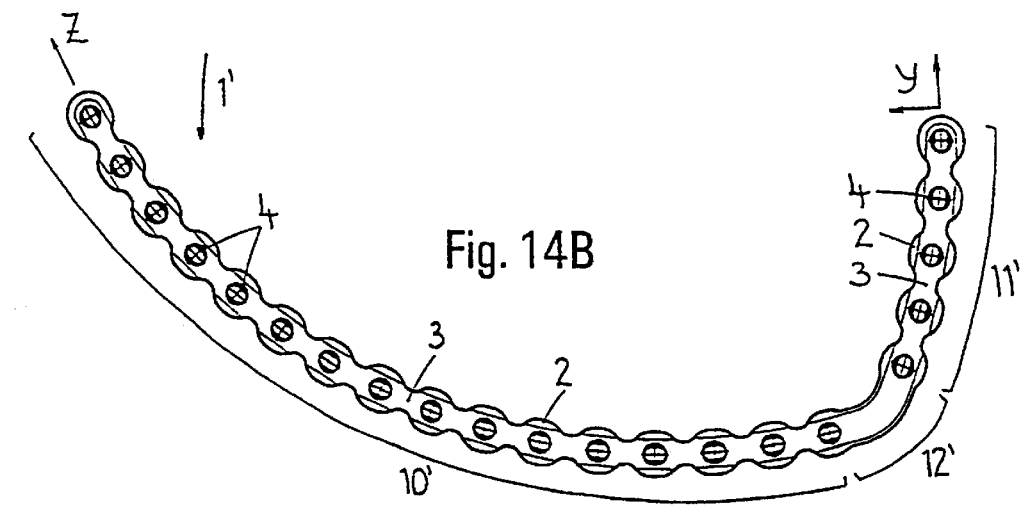
FIG. 14B shows the bone plate according to FIG. 14A with a curved lateral segment and a strengthened angle area without an additional screw hole.

This series of figures shows differently modified plates 1' with a longitudinal axis Z of the plate extending in the shape of an arc of a circle. All the plates 1' have a circular arc-shaped main segment 10' to which a lateral segment 11' is attached as an extension at the right end or left end or at both ends. The main segment 10' is here provided for example uniformly with 16 screw holes 4 suitable for blocking. At the transition between the main segment 10' and the lateral segment 11' there is an angled segment 12' which is strengthened preferably in width in relation to the webs 3. The angled segment 12' can be without holes (see FIGS. 14B and 14D) or can have at least one screw hole 4 (see FIGS. 14A, 14C and 14E). The lateral segment 11' can be straight in the plate plane Y (see FIGS. 14A, 14D and 14E) or curved (see FIGS. 14B and 14C). The modification according to FIG. 14E shows a plate 1' with a circular arc-shaped main segment 10' and a straight lateral segment 11' with reduced spacing between the 5 screw holes 4 shown, the angled segment 12' between these having one screw hole 4. In cases where a curved lateral segment 11' is provided at one end or at both ends of the circular arc-shaped main segment 10', said lateral segment 11' can have a bend radius different than the main segment 10'.

What is claimed is:

1. A blockable bone plate comprising:
   a plurality of plate members which are connected to each other via waist-like webs and lie on a plate plane in an unbent state;
   a bone screw hole in at least some plate members;
   one or more bone screws which can be introduced through the screw holes for securing the bone plate, wherein each bone screw has a screw head which is thickened in diameter, a blocking thread situated below the screw head, the blocking thread having a pitch angle, and a bone thread which extends at least partially over a screw shank, the screw shank having a smaller cross-sectional diameter than the screw head; and
   an engagement contour inside the screw hole for blocking of the bone plate by the blocking thread provided on the bone screw, wherein
   the engagement contour comprises contour valleys and adjacent contour peaks, which are arranged at least substantially horizontally and partially running peripherally on the wall of the screw hole,
   in relation to the plate plane, there is no orientation, as in the thread, between one contour valley and the next contour valley, and between one contour peak and the next contour peak,
   the valleys and peaks of the engagement contour do not extend at a pitch angle, and
   the blocking thread of the bone screw and the engagement contour of the screw hole are not complementary to each other.

2. The blockable bone plate as claimed in claim 1, wherein the screw hole has a spherical countersink on an upper surface of the plate for partially receiving a lower portion of the screw head for centering the bone screw, and having an oblong-shaped hole at an exit on a lower surface of the plate.

3. The blockable bone plate as claimed in claim 1, wherein the blocking thread of the bone screw includes at least one thread and can have a geometry different than or identical to the bone thread so the bone thread can be self-boring and/or self-tapping.

4. The blockable bone plate as claimed in claim 1 wherein the contour valleys and the contour peaks are oriented along a longitudinal axis of the plate or at an angle to the longitudinal axis.

5. The blockable bone plate as claimed in claim 1 wherein the engagement contour is similar to one of a pointed, a round, a trapezoidal, and a serrated thread.

6. The blockable bone plate as claimed in claim 2 wherein the engagement contour runs out at the horizontally located ends, so that wall areas remain in the screw hole and uncontoured wall areas lie on a theoretical main axis of the oblong-shaped screw hole in the area of the engagement contour.

7. The blockable bone plate as claimed in claim 1 wherein the bone screws are configured to be inserted into the screw holes vertically or with an angular offset in relation to a longitudinal axis of the plate and the plate plane.

8. The blockable bone plate as claimed in claim 1 further comprising bend edges developed by deformation on the blocking thread and on the engagement contour during blocking and providing increased security against the bone screw coming loose.

9. The blockable bone plate as claimed in claim 1 wherein a distance between adjacent contour valleys and contour peaks is in the range between 0.5 mm and 1.0 mm.

10. The blockable bone plate as claimed in claim 1 wherein the screw holes are configured such that bone screws without a blocking thread can be inserted vertically or obliquely into the screw holes.

11. The blockable bone plate as claimed in claim 1 wherein the longitudinal axis of the bone plate extending in the plate plane is at least substantially an arc of a circle.

12. The blockable bone plate as claimed in claim 11 wherein, as a result of the arc-shaped longitudinal axis of the plate, an offset of from about 1° to about 10° is obtained between the center axis of the webs and the center axis of the respectively adjacent screw hole.

13. The blockable bone plate as claimed in claim 11 wherein one or more screw holes is one of a cylindrical standard screw hole and an oriented compression screw hole.

14. The blockable bone plate as claimed in claim 11 wherein the bone plate further comprises a main segment with a plate longitudinal axis in an arc of a circle, a straight or curved lateral segment adjoining the main segment at at least one end, the lateral segment extending in the plate plane, and an angled segment extending in the plate plane between the main segment and the lateral segment.

15. The blockable bone plate as claimed in claim 14 wherein the angled segment is strengthened relative to the webs connecting the plate members and has no holes or has at least one of a screw hole including the engagement contour for blocking, a cylindrical standard screw hole, and an oriented compression hole and wherein the lateral segment is provided with at least one of screw holes having the engagement contour for blocking, cylindrical standard screw holes, and oriented compression screw holes.

16. The blockable bone plate as claimed claim in 11 wherein the arc of the bone plate is produced without deforming the bone plate.

17. The blockable bone plate as claimed in claim 11 wherein the bone plate is configured for the substantially horizontal, U-shaped engagement of the human jaw bone, in particular the lower jaw, where the ends of the bone plate, which consists only of a main segment or of one or two additional lateral segments, are dimensioned so as to engage over at least one ascending branch of the jaw.

18. A blockable bone plate comprising:
   a plurality of plate members which are connected to each other via waist-like webs and lie on a plate plane in an unbent state;
   a bone screw hole in at least some plate members;
   at least one bone screw which can be introduced through the screw holes for securing the bone plate, wherein at least one bone screw has a screw head, a blocking thread situated opposite the screw head, the blocking thread having a pitch angle, and a bone thread which extends at least partially over a screw shank, the screw shank having a smaller cross-sectional diameter than the screw head;

an engagement contour inside the screw hole for blocking of the bone plate by the blocking thread, wherein the engagement contour comprises contour valleys and adjacent contour peaks partially running peripherally on an inner wall of the screw hole, and, in relation to the plate plane, there is no orientation as a thread between one contour valley, and the next contour valley and between one contour peak and the next contour peak so that the valleys and peaks of the engagement contour do not extend at a pitch angle and the blocking thread of the bone screw and the engagement contour of the screw hole are not complementary to each other, the screw hole has a spherical countersink on an upper surface of the plate for partially receiving a lower portion of the screw head and for centering the bone screw, and is an oblong hole on a lower surface of the plate, and the engagement contour tapers and is absent at horizontally located ends of the hole, so that uncontoured wall areas of the screw hole lie on a theoretical main axis of the oblong hole.

19. The blockable bone plate as claimed in claim 18, wherein the blocking thread of the bone screw includes at least one thread geometrically different from or identical to the bone thread, so the bone thread can be self-boring and/or self-tapping.

20. The blockable bone plate as claimed in claim 18, wherein the contour valleys and the contour peaks are oriented along a longitudinal axis of the plate or at an angle to the longitudinal axis.

21. The blockable bone plate as claimed in claim 18, wherein the engagement contour is similar to one of a pointed, a round, a trapezoidal, and a serrated thread.

22. The blockable bone plate as claimed in claim 18, wherein the bone screws are configured to be inserted into the screw holes perpendicular to or with an angular offset in relation to a longitudinal axis of the bone plate and the plate plane.

23. The blockable bone plate as claimed in claim 18, further comprising bent edges developed by deformation on the blocking thread and on the engagement contour, during blocking, and providing increased security against the bone screw coming loose.

24. The blockable bone plate as claimed in claim 18, wherein distance between adjacent contour valleys and contour peaks is in the range between 0.5 mm and 1.0 mm.

25. The blockable bone plate as claimed in claim 18, wherein the screw holes are configured such that bone screws without blocking thread can be inserted into the screw holes.

26. The blockable bone plate as claimed in claim 18 wherein a longitudinal axis of the bone plate extending in the plate plane is at least substantially an arc of a circle.

27. The blockable bone plate as claimed in claim 26, wherein as a result of the circular arc-shaped longitudinal axis of the plate, an offset of from about 1° to about 10° is obtained between a center axis of the webs and a center axis of the respectively adjacent screw hole.

28. The blockable bone plate as claimed in claim 26, wherein at least one of the screw holes is one of a cylindrical standard screw hole and an oriented compression screw hole.

29. The blockable bone plate as claimed in claim 26 wherein the bone plate further comprises a main segment with a plate longitudinal axis in one of an arc of a circle, and a straight or curved lateral segment adjoining the main segment at at least one end, the lateral segment extending in the plate plane, and an angled segment extending in the plate plane between the main segment and the lateral segment.

30. The blockable bone plate as claimed in claim 29 wherein the angled segment is strengthened relative to the webs connecting the plate members and has no holes or has at least one of a screw hole including the engagement contour for blocking, a cylindrical standard screw hole, and an oriented compression hole, and wherein the lateral segment includes at least one of screw holes having the engagement contour for blocking, cylindrical standard screw holes, and oriented compression screw holes.

31. The blockable bone plate as claimed claim in 26 wherein the arc of the bone plate is produced without deforming the bone plate.

32. The blockable bone plate as claimed in claim 26 wherein the bone plate is configured for the substantially horizontal, U-shaped engagement of the human jaw bone, in particular the lower jaw, where ends of the bone plate, which consists only of a main segment or of one or two additional lateral segments, are dimensioned to engage more than at least one ascending branch of the jaw.

* * * * *